United States Patent [19]

Vince

[11] Patent Number: 4,950,276
[45] Date of Patent: Aug. 21, 1990

[54] PROSTHESIS FOR BANDING OF AN ARTERY CAPABLE OF DILATION BY A BALLOON DILATOR

[76] Inventor: Dennis J. Vince, 610 - 943 West Broadway, Vancouver, British Columbia, Canada, V5Z 1K3

[21] Appl. No.: 420,637

[22] Filed: Oct. 10, 1989

Related U.S. Application Data

[63] Continuation of Ser. No. 160,344, Feb. 25, 1988, abandoned.

[51] Int. Cl.$^5$ ............................................. A61B 17/08
[52] U.S. Cl. ..................................... 606/158; 606/157
[58] Field of Search ...................... 606/157, 158, 228; 623/12, 66, 1, 13, 14; 267/179, 180, 166; 604/281

[56] References Cited

U.S. PATENT DOCUMENTS

| | | | |
|---|---|---|---|
| 2,068,173 | 10/1934 | Galves | 128/327 X |
| 3,705,580 | 12/1972 | Gauthier | 128/327 X |
| 3,726,279 | 4/1973 | Barefoot et al. | 128/327 |
| 3,730,186 | 5/1973 | Edmunds, Jr. et al. | 128/327 X |
| 3,913,587 | 10/1975 | Newash | 623/66 X |
| 3,948,272 | 4/1976 | Guibor | 623/66 X |
| 4,130,904 | 12/1978 | Whalen | 623/1 |

FOREIGN PATENT DOCUMENTS

| | | | |
|---|---|---|---|
| 2065370 | 5/1973 | Fed. Rep. of Germany | 623/1 |
| 2620149 | 11/1977 | Fed. Rep. of Germany | 267/166 |
| 2929246 | 2/1980 | Fed. Rep. of Germany | 623/1 |
| 0020843 | 2/1981 | Japan | 267/166 |

OTHER PUBLICATIONS

D. J. Vince et al., *J. of Thoracic and Cardiovascular Surgery* (1987) vol. 93, No. 4 : 628–631.
D. J. Vince et al., *Radiology* (1987) 164 : 141–144.
D. J. Vince et al., *J. of Thoracic and Cardiovascular Surgery* (1989) vol. 97, No. 3 : 421–427.

*Primary Examiner*—Alan Cannon
*Attorney, Agent, or Firm*—Fetherstonhaugh & Co.

[57] ABSTRACT

A banding prosthesis comprising an expandable helical member encased within an elongatable outer covering. The ends of the outer covering are sealed and incorporate silk sutures for joining the two ends of the banding prosthesis to form a band about the circumference of a tubular organ such as a blood vessel so as to encircle and constrict the organ lumen. An intraluminal balloon dilator is inserted within the lumen of the organ in the region of the band and is inflated to dilate the banding prosthesis and allow the constricted lumen to expand. The design of the present invention allows for gradual dilation of the banding prosthesis in stages.

6 Claims, 1 Drawing Sheet

– 4,950,276 –

PROSTHESIS FOR BANDING OF AN ARTERY CAPABLE OF DILATION BY A BALLOON DILATOR

CROSS-REFERENCE TO RELATED APPLICATIONS

This is a continuation of application Ser. No. 160,344, filed Feb. 25, 1988 now abandoned.

FIELD OF THE INVENTION

This invention relates to a surgical device for banding an artery in order to constrict the flow through the artery, the device being subsequently expandable by use of a balloon dilator to reduce the constriction.

BACKGROUND OF THE INVENTION

Pulmonary artery banding is frequently used to treat infants with congenital heart malformations in whom the malformation results in excessive pulmonary blood flow. In current clinical practice, radiopaque umbilical tape, coated with medical adhesive silicon rubber, is widely used to band and constrict the pulmonary artery to reduce the blood flow. Such a fixed band, however, is not dilatable and therefore does not allow for the increased pulmonary blood flow necessary as the infant grows. As a result, further surgery is often necessary to either enlarge the constricting band or create an aorticopulmonary shunt around the constriction site. It will be appreciated that this additional surgery places a great deal of stress on the infant and correction of the initial defect is often made more difficult.

SUMMARY OF THE INVENTION

The present invention is a banding prosthesis to constrict an artery for an extended period of time and subsequently allow for dilation of the prosthesis while in place about the artery by an intraluminal balloon dilator thereby avoiding further operations.

Accordingly, the present invention is a banding prosthesis comprising an expandable helical member encased within an elongatable outer covering, the ends of said outer covering being sealed and incorporating attachment means for joining the two ends of the banding prosthesis to form a band about a diameter of a tubular organ such as a blood vessel so as to encircle and constrict said organ whereupon an intraluminal balloon dilator inserted within said organ in the region of said band and inflated can be used to dilate said banding prosthesis.

The present invention provides a safe and reliable banding prosthesis which can be dilated in stages while in place in a patient's body.

BRIEF DESCRIPTION OF THE DRAWINGS

A preferred embodiment of the present invention is shown in the accompanying drawings in which.

DESCRIPTION OF THE PREFERRED EMBODIMENTS

Figure 1:
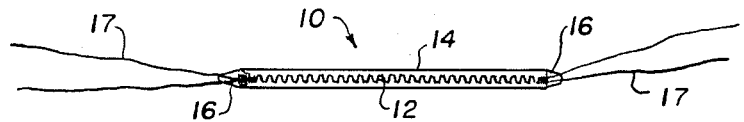
FIG. 1 shows the banding prosthesis of the present invention.

Referring to FIG. 1, there is shown a banding prosthesis 10 according to a preferred embodiment of the present invention. An expandable, helical member 12 is encased within a tubular, flexible and elongatable outer covering 14. In a preferred embodiment, helical member 12 is constructed using a stainless steel pacemaker electrode from a Medtronic (trademark) model 6957 pacemaker stretched to three times its original length. Outer covering 14 is made from silicon rubber tubing such as Silastic (trademark) medical-grade tubing.

Helical member 12 is inserted within the hollow inner core of covering 14 and the ends of the covering are sealed at 16 by silicone type A medical adhesive. Incorporated into the sealed ends 16 of covering 14 are attachment means 17 for joining the two ends of the prosthesis comprising double 3-0 silk sutures.

Figure 2:
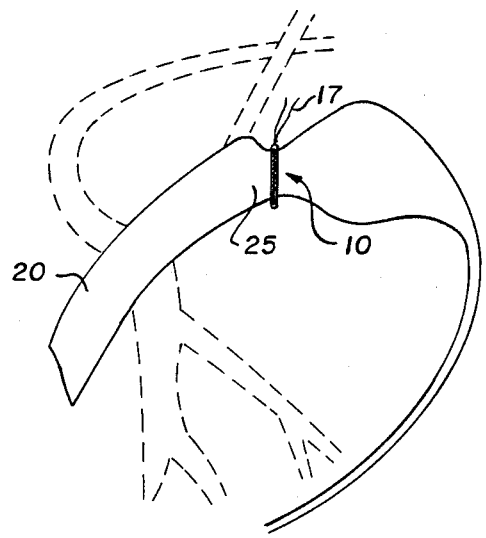
FIG. 2 shows the banding prosthesis in place about an artery of a dog.

In use, the banding prosthesis of the present invention is placed about an artery 20 as shown in FIG. 2. Sutures 17 are tied together to form a constricting band to reduce the cross-sectional area of the artery available for blood flow. In a series of animal experiments on dogs, it was found that the prosthesis of the present invention could constrict an artery for a prolonged period, up to 129 days, without stretching and subsequently be capable of dilation by an intraluminal balloon dilator.

Figure 3:
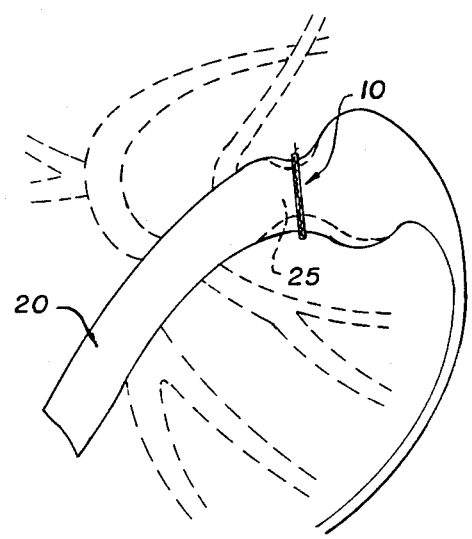
FIG. 3 shows the banding prosthesis of FIG. 2 after dilation by a balloon dilator.

FIG. 3 shows the banding prosthesis after dilation by a balloon dilator. A conventional balloon dilator comprising an inflatable balloon portion and an inflation tube is inserted into the artery 20. The balloon dilator is manoeuvered through the artery in an uninflated state into constricted region 25 defined by the banding prosthesis 10. The progress of the balloon dilator in the artery can be observed using an image intensifier so that direct access to the operation site is not necessary. Upon inflation of the balloon portion of the balloon dilator, the outward expansion of the balloon acts against the banding prosthesis to permanently uncoil helix member 12 and stretch elongatable outer covering 14 so as to increase diameter of the constricted region 25 as shown in FIG. 3. In the animal experiments conducted, inflation of the balloon to six atmospheres pressure was necessary to expand the banding prosthesis. Outer covering 14 prevented tissue ingrowth into helical member 12 which would tend to prevent uncoiling of the helical member.

The banding prosthesis of the present invention can be expanded in stages using different sized balloon dilators. Each expansion procedure acts to partially uncoil helix member 12 and stretch elongatable outer covering 14. Once expanded to a larger size, helix member 12 maintains the new dilation. It is possible to accurately expand the applied prosthesis to a given diameter by using a balloon dilator having a known maximum dilatable diameter.

The present invention thus provides a safe and reliable banding prosthesis capable of constricting an artery and being subsequently dilated in stages by an intraluminal balloon dilator.

I claim:

1. A banding prosthesis comprising an expandable helical member having a series of coils that define a cylindrical volume having an outer surface, said outer surface being encased by an elongatable outer covering having a pair of sealed ends to completely enclose the cylindrical volume of said helical member said ends of said outer covering incorporating attachment means for joining the two ends of the banding prosthesis to form an encircling band about a circumference of a tubular organ so as to constrict the organ lumen whereupon an intraluminal balloon dilator inserted within the lumen of said organ in the region of said band and inflated can be used to permanently dilate said banding prosthesis and allow the constricted lumen to expand.

2. A banding prosthesis as claimed in claim 1 wherein said expandable helical member is made from stainless steel.

3. A banding prosthesis as claimed in claim 1 wherein said elongatable outer covering is formed from a tubular member of silicone rubber.

4. A banding prosthesis as claimed in claim 1 in which said ends of said outer covering are sealed with silicone type A medical adhesive.

5. A banding prosthesis as claimed in claim 1 wherein said attachment means for joining the ends comprises double silk sutures.

6. A banding prosthesis as claimed in claim 5 wherein said sutures are made from 3-0 silk.

* * * * *